US00PP09754P

United States Patent [19]

Suzuki et al.

[11] Patent Number: Plant 9,754

[45] Date of Patent: Dec. 17, 1996

[54] PETUNIA PLANT NAMED 'SUNBERUBU'

[75] Inventors: Kenichi Suzuki, Ibaraki; Yoshiji Nishikawa, Yamanashi; Yasuyuki Murakami, Kofu, all of Japan

[73] Assignee: Suntory Limited, Osaka, Japan

[21] Appl. No.: 416,071

[22] Filed: Apr. 3, 1995

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

| | | | |
|---|---|---|---|
| P.P. 6,899 | 7/1989 | Tsuda et al. | Plt./68.1 |
| P.P. 6,914 | 7/1989 | Tsuda et al. | Plt./68.1 |
| P.P. 6,915 | 7/1989 | Tsuda et al. | Plt./68.1 |
| P.P. 8,489 | 12/1993 | Hirabayashi et al. | Plt./68.1 |
| P.P. 8,768 | 7/1994 | Hirabayashi et al. | Plt./68.1 |
| P.P. 9,322 | 10/1995 | Tachibana et al. | Plt./68.1 |
| P.P. 9,341 | 10/1995 | Tachibana et al. | Plt./68.1 |
| P.P. 9,342 | 10/1995 | Sakazaki et al. | Plt./68.1 |
| P.P. 9,556 | 5/1996 | Tachibana et al. | Plt./68.1 |
| P.P. 9,557 | 5/1996 | Suzuki et al. | Plt./68.1 |

*Primary Examiner*—James R. Feyrer

*Attorney, Agent, or Firm*—Burns, Doane, Swecker & Mathis, L.L.P.

[57] ABSTRACT

Disclosed herein is a petunia plant having a intermediate habit type between upright habit type and decumbent habit type. The plant has abundant branching and a great profusion of blooms, and the whole bush remains in bloom for a long period of time. The flowers are single and very small, and the petals have a vivid reddish purple color and vivid greenish yellow throat inside portion. The plant is highly resistant to cold, rain, heat, and disease.

4 Drawing Sheets

BACKGROUND OF THE VARIETY

The present invention relates to a new and distinct variety of petunia plant obtained from crossing one petunia plant (♀) 'PV25' having purple petal which was selected from a crossing of a wild type of petunia plant native to Brazil, and one petunia plant (♂) 'PV15' having purple petal (but, different from the female parent) which was selected from a crossing of a wild type of petunia plant native to Brazil.

The petunia is a very popular plant and is used for flower bedding and potting in the summer season. There are only a few varieties of the petunia plant which do not have an upright growth habit and which have a high resistance to rain, heat, cold, and diseases. The petunia which we previously filed, i.e. the Revolution series [('Revolution Purplepink' (U.S. Pat. No. Plant 6,915), 'Revolution Brilliantpink' (U.S. Pat. No. Plant 6,914), and 'Revolution Brilliantpink'-mini (U.S. Pat. No. Plant 6,899)] is a decumbent type plant having long stems, a lower plant height, abundant branching, and a high resistance to heat, cold and rain. However, there are only a few varieties having a great profusion of flowers with a very small flower diameter, and a high resistance to rain, heat, cold, and disease. Accordingly, this invention was aimed at obtaining a new variety having a vivid purple color petal, together with the above features.

Four plants of a few wild types of petunia plants from Brazil, having flowers with a small flower diameter were selected, in view of plant form, flower color, and flower bloom. The selected plants were propagated in January, 1990 at the Plant Biotechnology Laboratory, Institute for Fundamental Research of Suntory Ltd., residing at 2913-1 Torihara, Hakushu-cho, Kitakoma-gun, Yamanashi-ken, Japan, interspecies crossing of flowering plants was begun from May 1990, and then, by January, 1991, 300 plants obtained by interspecific crosses were obtained. 12 plants were selected from this crossing, each was manually self-pollinated, and 1000 plants resulting from such pollination were obtained in January, 1992. From these, 20 plants were selected by a pot trial. The selected 20 plants were propagated by cutting, and then grown in bed and pot on trail from May, 1992. Finally only one of the 20 resulting plants was selected. The botanical characteristics of the finally-selected plant were then examined, using a similar variety, 'Pearl Skyblue', for comparison. As a result, it was concluded that this petunia plant is distinguishable from any other variety, whose existence is known to us, and this new variety of petunia plant was initially designated 'SP-B ', and subsequently was named —'Sunberubu'.

In the following description, the color-coding is in accordance with *The R.H.S. Colour Chart* of The Royal Horticultural Society, London, England, and *The Inter-Society Color Council-National Bureau of Standards Color Names* (I.S.C.C.-N.B.S. Color Name). A color chart based on *The Japan Color Standard for Horticultural Plants* (J.H.S. Color Chart) is also added for reference.

The female parent used in the breeding of 'Sunberubu'is a petunia plant having a purple petal which was selected from a crossing of a wild type of petunia plant native to Brazil, the seeds of this was gathered at Gramado, Rio Grando Do Sul, Brazil and introduced to Japan in October, 1983. This wild type of plant is presently maintained at the aformentioned Plant Biotechnology Laboratory of Suntory Ltd. The main botanical characteristics of this female parent 'PV25' are as follows.

Grow habit: Erect—Medium

Plant height: 16 cm.

Spreading area of plant: The stem extends to a length of 11 cm from the base, and thus the spreading area of the plant is 21 cm in diameter.

Growth: Vigorous with abundant branching, profusion of bloom.

Blooming period: April to September, in all areas of Japan. The plant shape does not change throughout this period.

Stem: Extending to 11 cm.

*Thickness.*—1.7 mm.

*Anthocyanin pigmentation.*—Absent.

*Pubescence.*—Medium.

*Branching.*—Few — Medium (primary), over-abundant (secondary), spreading by rooting at the base of stems.

*Length of internode.*—14 mm.

Leaf:

*Leaf attaching angle.*—Horizontal.

*Shape.*—Lanceolate.

*Length.*—3.6 cm.

*Width.*—1.3 cm.

*Color.*—Deep yellow green (J.H.S. No. 3707).

*Pubescence.*—Few.

*Petiole of main stem.*—Absent.

Flower:

*Facing direction.*—Horizontal, and slightly slanting upward.

*Type.*—Single.

*Shape.*—Funnel-shape, with five fused segments.

*Diameter.*—27 mm.

*Color.*—Vivd bluish purple (J.H.S. No. 8306, R.H.S. No. 88A), bottom throat inside portion vivid greenish yellow (J.H.S. No. 2906), throat outside portion strong reddish purple (J.H.S. No. 8911, R.H.S. No. 77B, fading of petal color is very weak.

Reproductive organs: 1 normal pistil and 5 normal stamens. Pistil is narrow shape and stamens are narrow shape.

Peduncle: 1.7 cm in length.

The pollen parent used in the breeding of 'Sunberubu'is a petunia plant having a purple petal, different from the female parent, which was selected from a crossing of a wild type of petunia plant native to Brazil, the seeds of this were gathered at Gramado, Rio Grando Do Sul, Brazil and introduced to Japan in October, 1983. This wild type of plant is presently maintained at the aforementioned Plant Biotechnology Laboratory of Suntory Ltd. The main botanical characteristics of the male parent, 'PV15' are as follows.

Growth habit: Erect. The branches erect from the base of stem.

Plant height: 18 cm.

Spreading area of plant: The stem extends to a length of 13 cm from the base, and thus the spreading area of the plant is 18 cm in diameter.

Growth: Vigorous with abundant branching, profusion of bloom.

Blooming period: April to September, in all areas of Japan. The plant shape does not change throughout this period.

Stem: Extending to 13 cm.

*Thickness.*—1.5 mm.

*Anthocyanin pigmentation.*—Absent.

*Pubescence.*—Medium.

*Branching.*—Few (primary), over-abundant (secondary), spreading by rooting at the base of stems.

*Length of internode.*—14 mm.

Leaf:

*Leaf attaching angle.*—Horizontal, and slightly slanting upward.

*Shape.*—Lanceolate.

*Length.*—3.4 cm.

*Width.*—1.1 cm.

*Color.*—Deep yellow green (J.H.S. No. 3707).

*Pubescence.*—Few.

*Petiole of main stem.*—Absent

Flower:

*Facing direction.*—Horizontal.

*Type.*—Single.

*Shape.*—Funnel-shape, with five fused segments.

*Diameter.*—24 mm.

*Color.*—Vivid bluish purple (J.H.S. No. 8306, R.H.S. No. 87A), fading of petal color at blooming line is a little bit strong, and faded color is bright bluish purple (J.H.S. No. 8305, R.H.S. No. 88C), bottom throat inside portion vivid greenish yellow (J.H.S. No. 2906), throat outside portion strong reddish purple (J.H.S. No. 8911, R.H.S. No. 77B).

Reproductive organs: 1 normal pistil and 5 normal stamens. Pistil is narrow shape and stamens are narrow shape.

Peduncle: 1.6 cm in length.

This new and distinct variety of petunia plant, 'Sunberubu', was asexually reproduced by cuttings at the aforementioned Plant Biotechnology Laboratory, Institute for Fundamental Research of Suntory Ltd., residing at 2913-1 Torihara, Hakushu-cho, Kitakoma-gun, Yamanashi-ken, Japan, and the homogeneity and stability thereof were confirmed.

SUMMARY OF THE VARIETY

The new variety of petunia plant has an intermediate growth habit between upright habit and decumbent habit, which is almost similar to 'Pearl Skyblue' (non-patented in the United States). The plant has a great profusion of flowers with a very small diameter, and very small stem thickness, which are much smaller than these of the similar variety, 'Pearl Skyblue'. The length of internode of the new variety is longer than that of 'Pearl Skyblue'. The flowers of the new variety are single, and very small, the petal has a vivid purple color, and the bottom throat inside portion of the corolla has a vivid greenish yellow color, which are distinguishable from the similar variety, 'Pearl Skyblue'.

The plant is highly resistant to rain, heat, cold, and diseases.

DESCRIPTION OF THE VARIETY

Figure 1:
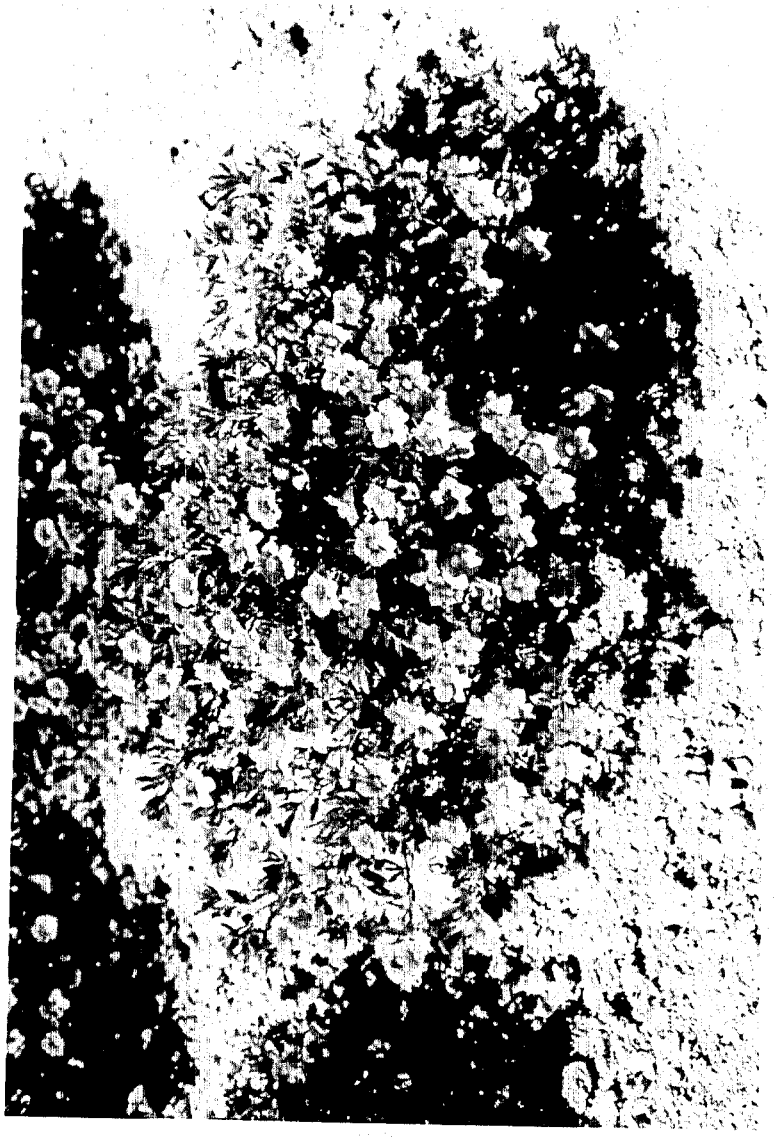
FIG. 1 is a photograph giving a partial view of the new variety of petunia plant planted in a flower bed.
Figure 2:
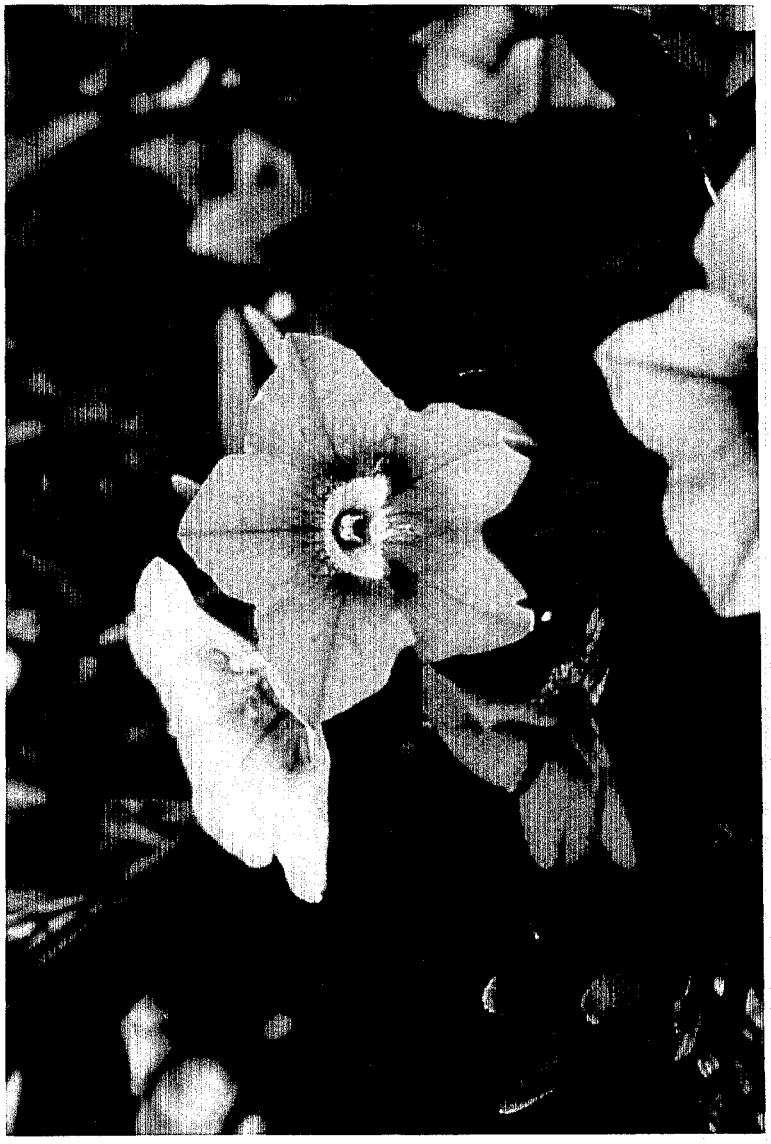
FIG. 2 is a photograph of flowers of the new variety of petunia plant.
Figure 3:
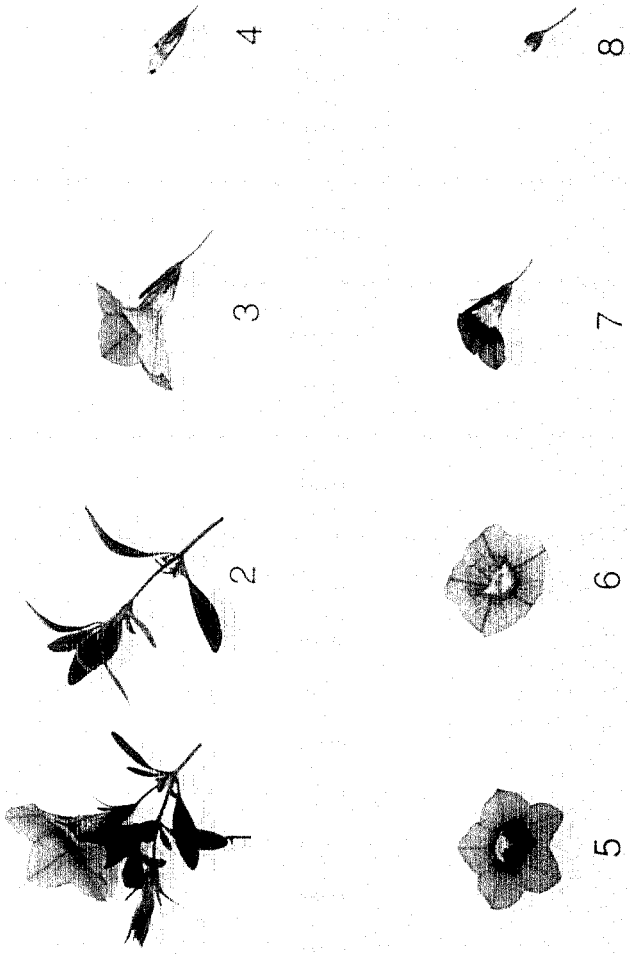
FIG. 3 is a photograph showing, in numerical order, a flower cluster (1), a current shoot (2), a flower (3), a bud (4), a front view of a petal (5), a rear view of a petal (6), a cross-sectional view of the flow (7), and pistil and stamens (8)
Figure 4:
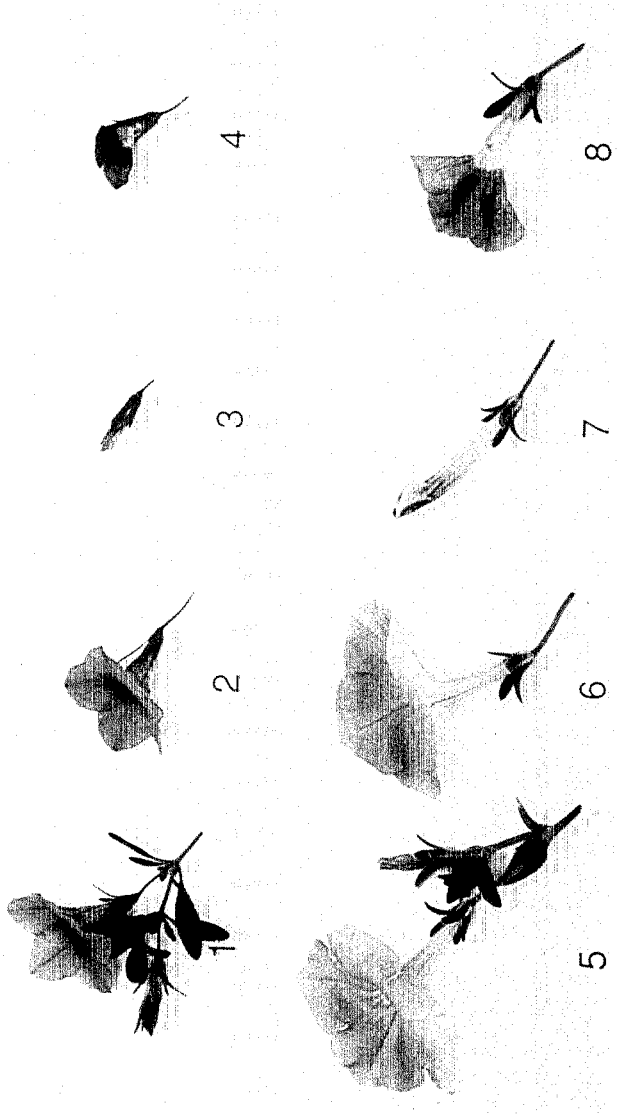
FIG. 4 is a photograph showing, in numerical order, a flower cluster (1), a flower (2), a bud (3), and a cross-sectional view of the flower (4) of the new variety of petunia plant, in comparison with corresponding items (5 to 8) of a similar variety 'Pearl Pink'.

The botanical characteristics of the new and distinct variety of petunia plant 'Sunberubu' are as follows.

Plant:

*Growth habit.* 'Intermediate. The branches spread from the base of a stem obliquely upward.

*Plant height.*—20 cm.

*Spreading area of plant.*—The stem extends to a length of 11 cm from the base, and thus the spreading area of the plant is 30 cm in diameter.

*Growth.*—Very vigorous with abundant branching, a great profusion of bloom; the whole bush remaining in bloom for a considerable period of time.

*Blooming period.*—Late March to the beginning of October, in all areas of Japan. The plant shape does not change throughout this period.

Stem: Extending to 11 cm.

*Thickness.*—1.5 mm.

*Anthocyanin pigmentation.*—Absent.

*Pubescence.*—Medium.

*Branching.*—Medium (primary), over-abundant (secondary), spreading by rooting at the base of stems.

*Length of internode.*—15 mm.

Leaf:

*Leaf attaching angle.*—Horizontal.

*Shape.*—Lanceolate.

*Length.*—3.2 cm.

*Width.*—1.3 cm.

*Color.*—deep yellow green (J.H.S. 3707).

*Pubescence.*—Few.

*Petiole of main stem.*—Absent.

Flower:

*Facing direction.*—Horizontal.

*Type.*—Single.

*Shape.*—Funnel-shape, with five fused segments.

*Diameter.*—25–30 mm.

*Color.*—Vivid purple (R.H.S. 81A, J.H.S. 8606) fading of petal color at blooming line is strong, and faded color is bright purple (J.H.S. 8604, R.H.S. No. 81C), bottom throat inside portion vivid greenish yellow (J.H.S. 2906), throat outside portion light yellow green (R.H.S. 2D, J.H.S. 3103).

*Reproductive organs.*—1 normal pistil and 5 normal stamens (2 stamens are higher than pistil). Pistil is narrow shape and stamens are narrow shape.

*Peduncle.*—1.8 cm in length.

Physiological and ecological characteristics: High resistance to cold, rain, and heat. Moderate resistance to diseases and pests.

This new variety of petunia plant is most suitable for flower bedding and potting, particularly in hanging pots or planters, and further excellent for ground cover.

The plant of this new variety 'Sunberubu' is presently planted and maintained at the Plant Biotechnology Laboratory, Institute for Fundamental Research of Suntory Ltd., residing at 2913-1 Torihara, Hakushu-cho, Kitakoma-gun, Yamanashi-ken, Japan.

We claim:

1. A new and distinct variety of petunia plant, substantially as herein illustrated and described, characterized particularly as to novelty by (A) an abundant branching and a great profusion of blooms, the whole bush remaining in bloom for a considerable period of time, (B) flowers that are single and very small, the petals having a vivid purple color and vivid greenish yellow throat inside portion, and (C) a high resistance to cold, rain, heat, and disease.

* * * * *